(12) United States Patent  (10) Patent No.: US 7,446,332 B2
Yasuda  (45) Date of Patent: *Nov. 4, 2008

(54) RADIATION IMAGE READ-OUT APPARATUS AND RADIATION IMAGE CONVERTOR PANEL

(75) Inventor: Hiroaki Yasuda, Kaisei-machi (JP)

(73) Assignee: Fujifilm Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/694,692

(22) Filed: Mar. 30, 2007

(65) Prior Publication Data

US 2007/0164242 A1   Jul. 19, 2007

Related U.S. Application Data

(63) Continuation of application No. 10/718,643, filed on Nov. 24, 2003.

(30) Foreign Application Priority Data

Nov. 25, 2002  (JP) ............................. 2002-340972

(51) Int. Cl.
  *G03B 42/08* (2006.01)
(52) U.S. Cl. ...................................... 250/586
(58) Field of Classification Search .................. 250/586
  See application file for complete search history.

(56) References Cited

U.S. PATENT DOCUMENTS

| 4,755,672 | A | 7/1988 | Watanabe et al. |
| 4,896,043 | A | 1/1990 | Arakawa et al. |
| 4,944,026 | A | 7/1990 | Arakawa et al. |
| 5,596,202 | A | 1/1997 | Arakawa |
| 5,905,014 | A * | 5/1999 | Van de Bergh ............... 430/139 |
| 6,583,434 | B2 * | 6/2003 | Struye et al. ................. 250/581 |
| 6,985,170 | B1 | 1/2006 | Tsuyuki |
| 7,242,018 | B2 * | 7/2007 | Yasuda ........................ 250/584 |
| 2003/0042445 | A1 | 3/2003 | Mitchell et al. |
| 2003/0179415 | A1 | 9/2003 | Yasuda |

FOREIGN PATENT DOCUMENTS

| JP | 60-234643 | 11/1985 |
| JP | 62-169099 | 7/1987 |
| JP | 1-194749 | 8/1989 |
| JP | 2-213803 | 8/1990 |
| JP | 05-122774 | 5/1993 |
| JP | 8-087085 | 4/1996 |
| JP | 2000-137172 | 5/2000 |
| JP | 2002-107848 | 4/2002 |

* cited by examiner

*Primary Examiner*—Constantine Hannaher
(74) *Attorney, Agent, or Firm*—Sughrue Mion, PLLC

(57) ABSTRACT

A radiation image read-out apparatus includes a condenser optical system which converges stimulated emission emitted from a radiation image convertor panel upon exposure to stimulating light. A photodetector receives the stimulated emission converged by the condenser optical system and has a sensitivity to light longer in wavelength than the stimulating light and a stimulating light cut filter is disposed in the optical path of the stimulated emission between the photodetector and the radiation image convertor panel to transmit the stimulated emission and to cut the stimulating light. A longer wavelength light cut filter which transmits the stimulated emission and attenuates the intensity of light components longer in wavelength than the stimulating light is provided in the optical path of the stimulated emission between the photodetector and the radiation image convertor panel.

1 Claim, 6 Drawing Sheets

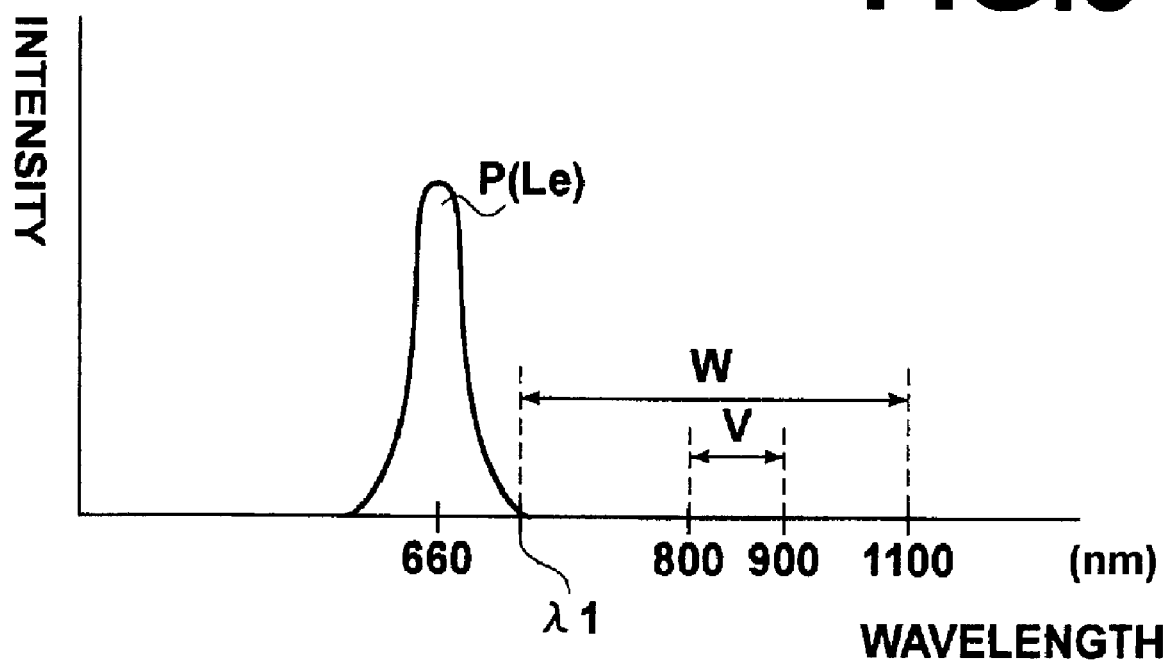

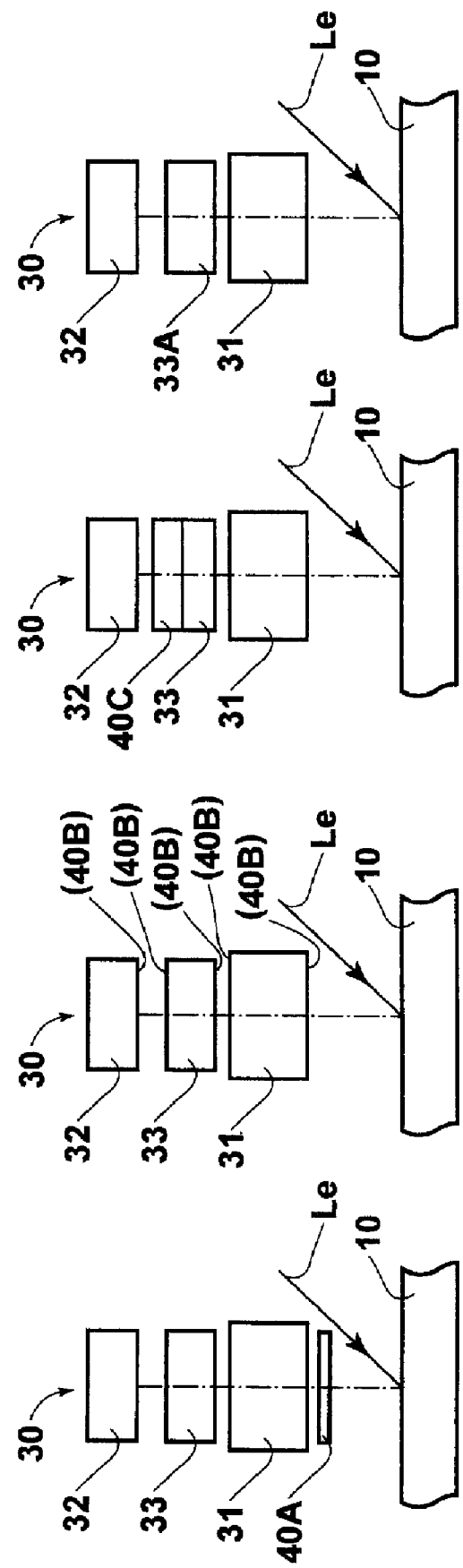

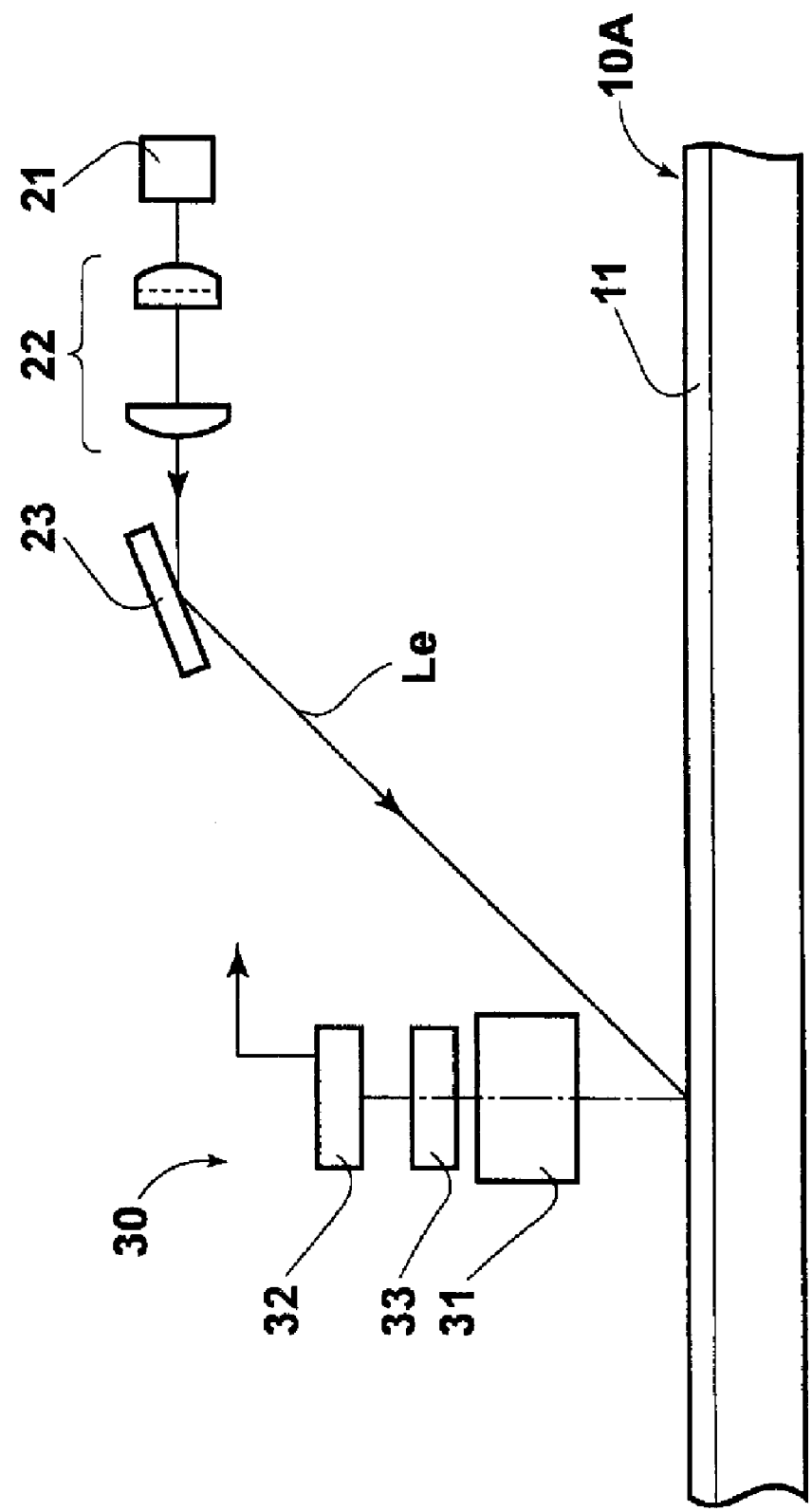

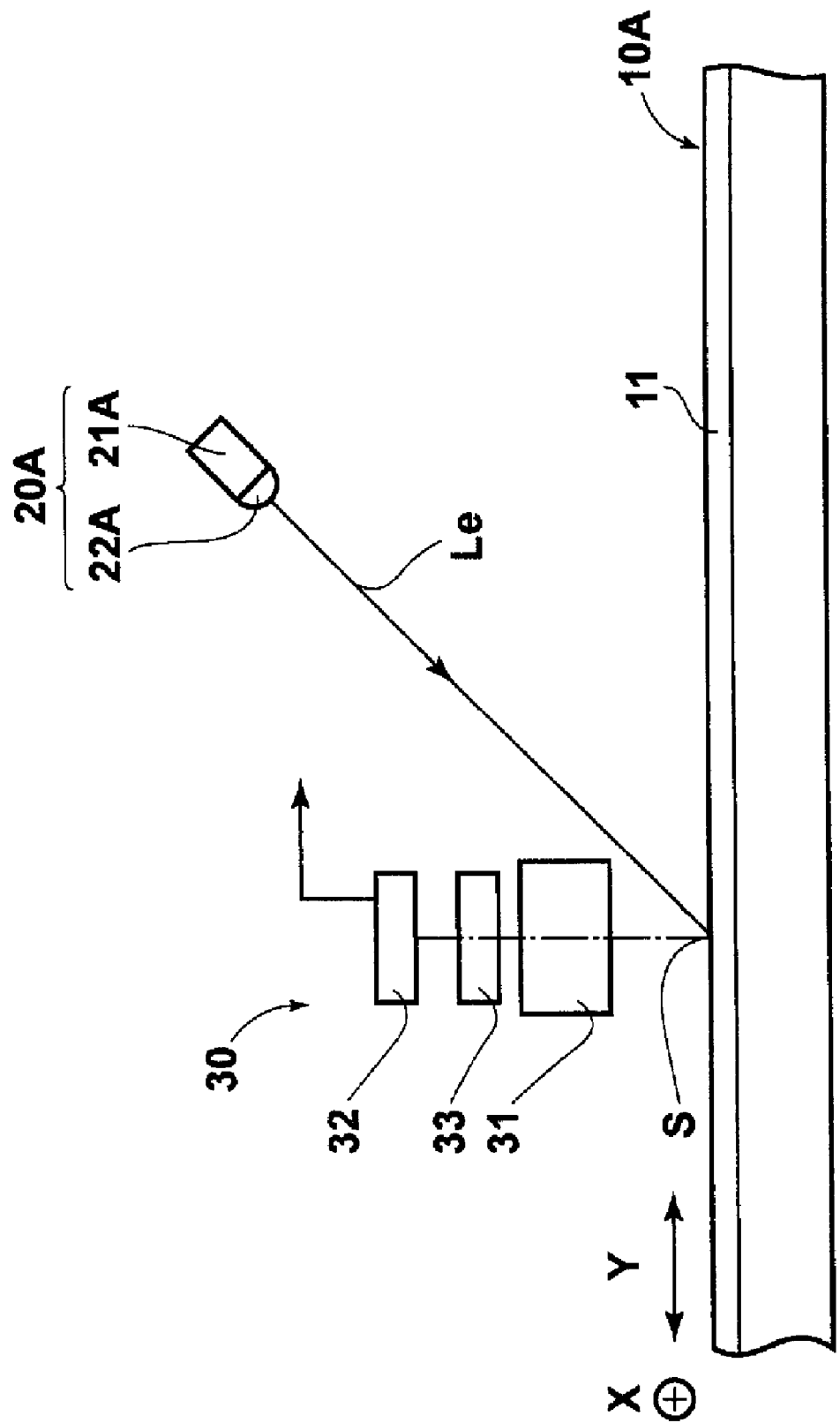

RADIATION IMAGE READ-OUT APPARATUS AND RADIATION IMAGE CONVERTOR PANEL

This is a continuation of application Ser. No. 10/718,643 (confirmation no. 1194) filed Nov. 24, 2003. The entire disclosure of the prior application, application Ser. No. 10/718,643, is hereby incorporated by reference.

BACKGROUND OF THE INVENTION

1. Field of the Invention

This invention relates to a radiation image read-out apparatus and a radiation image convertor panel, and more particularly to a radiation image read-out apparatus in which stimulated emission emitted from a radiation image convertor panel upon exposure to stimulating light is detected by a photodetector and a radiation image convertor panel to be used in the radiation image read-out apparatus.

2. Description of the Related Art

When certain kinds of phosphors are exposed to radiation such as X-rays, they store a part of energy of the radiation. Then when the phosphors which have been exposed to the radiation are exposed to stimulating light such as visible light, light having a wavelength shorter than the stimulating light is emitted from the phosphors in proportion to the stored energy of the radiation. Phosphors exhibiting such properties are generally referred to as "stimulable phosphors". In this specification, the light emitted from the stimulable phosphors upon stimulation thereof will be referred to as "stimulated emission". There has been known as a CR (computed radiography) a radiation image recording and reproducing system, comprising a radiation image recording apparatus and a radiation image read-out apparatus, in which a layer of the stimulable phosphors is exposed to a radiation passing through an object such as a human body to have a radiation image of the object once stored on the stimulable phosphor layer as a latent image, stimulating light such as a laser beam is subsequently projected onto the stimulable phosphor layer, and the stimulated emission emitted from the stimulable phosphor layer is photoelectrically detected, thereby obtaining an image signal (a radiation image signal) representing a radiation image of the object. There has been known a radiation image convertor panel comprising a stimulable phosphor layer formed on a substrate as a recording medium employed in the radiation image recording and reproducing system.

There has been known a radiation image read-out apparatus in which red stimulating light emitted from a semiconductor laser is projected onto a radiation image convertor panel and stimulated emission emitted from the radiation image convertor panel upon exposure to the red stimulating light is detected by a photomultiplier through a stimulating light cut filter which transmits the stimulated emission and cuts the red stimulating light, whereby a radiation image signal representing a radiation image recorded on the radiation image convertor panel is obtained.

Though the red stimulating light emitted from the semiconductor laser is cut by the stimulating light cut filter, components of the light emitted from the semiconductor laser longer than the red stimulating light in wavelength can pass through the stimulating light cut filter to impinge upon the photomultiplier. However since being very low in sensitivity to light longer in wavelength than the red region, the photomultiplier never detects light components longer in wavelength than the red region when detecting stimulated emission which is shorter than the stimulating light in wavelength.

In an attempt to meet a demand for miniaturization of the radiation image read-out apparatus, there has been studied an apparatus in which stimulated emission emitted from a radiation image convertor panel is imaged on a line sensor formed by a number of CCD elements and an image signal representing a radiation image recorded on the radiation image convertor panel is obtained through the line sensor.

Since being formed by a diode having a sensitivity to light longer in wavelength than the stimulating light, the CCD element has a sensitivity to not only a visible region but also light longer in wavelength than the red region and detects light components longer than the red stimulating light in wavelength passing through the stimulating light cut filter to impinge upon the line sensor, whereby signal components representing the longer side light components can mix in the image signal as a noise component. Further, these inventor's analysis has revealed that the longer side light components which can generate a noise component in the image signal include the following components.

(1) Those generated from the stimulating light source together with the stimulating light.
(2) Those generated from a radiation image convertor panel exposed to the stimulating light and believed to be mainly of fluorescence.
(3) Those generated from a condenser lens exposed to the stimulating light and believed to be mainly of fluorescence.
(4) Those generated from foreign matter adhering to the radiation image convertor panel and/or the condenser lens exposed to the stimulating light and believed to be mainly of fluorescence.

Those of (2) and (3) are equivalent to the intensity of stimulated emission emitted from a radiation image convertor panel exposed to radiation of several mr, and those of (4) are equivalent to the intensity of stimulated emission emitted from a radiation image convertor panel exposed to radiation of several tens mr. Accordingly, it is required to attenuate the intensity of the light components longer in wavelength than the stimulating light to preferably not higher than $1/100$ and more preferably not higher than $1/1000$. Further, it has been found that the main part of the light components longer in wavelength than the stimulating light is in the range not shorter than 800 nm and not longer 900 nm in wavelength.

This problem is involved not only when the stimulated emission is detected by the CCD elements but also when the stimulated emission is detected by other photodetectors which have a sensitivity to light longer in wavelength than the stimulating light.

SUMMARY OF THE INVENTION

In view of the foregoing observations and description, the primary object of the present invention is to provide a radiation image read-out apparatus and a radiation image convertor panel which can reduce the intensity of the light components longer in wavelength than the stimulating light.

In accordance with a first aspect of the present invention, there is provided a radiation image read-out apparatus which comprises a condenser optical system which converges stimulated emission emitted from a radiation image convertor panel upon exposure to stimulating light, a photodetector which receives the stimulated emission converged by the condenser optical system for photoelectric conversion and has a sensitivity to light longer in wavelength than the stimulating light and a stimulating light cut filter which is disposed in the optical path of the stimulated emission between the photodetector and the radiation image convertor panel to transmit the stimulated emission and to cut the stimulating light, and reads out a radiation image recorded on the radiation image convertor panel, wherein the improvement comprises that a longer wavelength light cut filter which transmits the stimulated emission and attenuates the intensity of light components longer in wavelength than the stimulating light is provided in the optical path of the stimulated emission between the photodetector and the radiation image convertor panel.

It is preferred that the longer wavelength light cut filter be disposed between the condenser optical system and the photodetector.

For example, the longer wavelength light cut filter attenuates the intensity of the light components in the range not shorter than 800 nm and not longer 900 nm in wavelength to preferably not higher than $1/100$ and more preferably not higher than $1/1000$. Further, it is preferred that the longer wavelength light cut filter transmits the stimulated emission at a transmissivity of not lower than 70%.

The radiation image read-out apparatus of the present invention may further comprise a correction means which subtracts an image signal component which represents a light component longer in wavelength than the stimulating light passing through the longer wavelength light cut filter and is included in an image signal obtained by photoelectric conversion of the stimulated emission by the photodetector from the image signal, thereby correcting the image signal. The correction need not be limited to a correction in which the image signal components representing light components longer in wavelength than the stimulating light are all subtracted from the image signal but may include corrections in which only a part of the image signal components representing light components longer in wavelength than the stimulating light is subtracted from the image signal.

The longer wavelength light cut filter may be provided, for instance, by providing an optical member which absorbs or reflects light components longer in wavelength than the stimulating light, applying an optical coating which reflects such light components to the light inlet or light outlet face of the condenser optical system, forming the elements of the condenser optical system of material which absorbs such light components, applying an optical coating which reflects such light components to the light inlet or light outlet face of the stimulating light cut filter, forming the stimulating light cut filter of material which also absorbs such light components so that the stimulating light cut filter doubles as the longer wavelength light cut filter, applying an optical coating which reflects such light components to the light inlet face of the photodetector, or forming a light inlet window of the photodetector of material which absorbs such light components.

In accordance with a second aspect of the present invention, there is provided a radiation image convertor panel which emits stimulated emission upon exposure to stimulating light, wherein the improvement comprises that a longer wavelength light cut filter which transmits the stimulating light and the stimulated emission and attenuates the intensity of the light components longer in wavelength than the stimulating light is provided on the side of the radiation image convertor panel from which the stimulated emission emitted from the radiation image convertor panel is detected.

For example, the longer wavelength light cut filter attenuates the intensity of the light components in the range not shorter than 800 nm and not longer 900 nm in wavelength to preferably not higher than $1/100$ and more preferably not higher than $1/1000$. Further, it is preferred that the longer wavelength light cut filter transmits the stimulated emission at a transmissivity of not lower than 70%.

The expression "light components longer in wavelength than the stimulating light" means light components which are longer in wavelength than a wavelength at which the intensity of the stimulating light is $1/100$ of the peak intensity of the stimulating light on the side longer in wavelength than the wavelength at which the stimulating light exhibits the peak intensity within the range where the photodetector has a sensitivity.

The expression "the longer wavelength light cut filter attenuates the intensity of the light components longer in wavelength than the stimulating light" means that the longer wavelength light cut filter attenuates at least a part of such light components, and it is preferred that the longer wavelength light cut filter attenuates such light components to such an extent that substantially no problem is involved. The longer wavelength light cut filter may attenuate the intensity of the light components longer in wavelength than the stimulating light by absorbing or reflecting such light components, or by a different system.

In the radiation image read-out apparatus of the present invention, by virtue of the longer wavelength light cut filter, the intensity of light components longer than the stimulating light impinging upon the photodetector is attenuated and noise mixing in the image signal representing the radiation image recorded on the radiation image convertor panel can be reduced.

When the longer wavelength light cut filter is disposed between the condenser optical system and the photodetector, also light components emitted from the condenser optical system longer than the stimulating light can be attenuated.

When the longer wavelength light cut filter attenuates the intensity of the light components in the range not shorter than 800 nm and not longer 900 nm in wavelength to not higher than $1/100$, the main part of the light components longer in wavelength than the stimulating light can be attenuated.

When the radiation image read-out apparatus of the present invention further comprises a correction means which subtracts an image signal component which represents a light component longer in wavelength than the stimulating light passing through the longer wavelength light cut filter and is included in an image signal obtained by photoelectric conversion of the stimulated emission by the photodetector from the image signal, thereby correcting the image signal, offset components included in the image signal component representing the light component longer in wavelength than the stimulating light included in the image signal can be removed, whereby an image signal representing the density of the radiation image with a more accurate linearity can be obtained.

In the radiation image convertor panel of the present invention, by virtue of the longer wavelength light cut filter, the intensity of light components longer than the stimulating light impinging upon the photodetector is attenuated and noise mixing in the image signal representing the radiation image recorded on the radiation image convertor panel can be reduced.

When the longer wavelength light cut filter attenuates the intensity of the light components in the range not shorter than 800 nm and not longer 900 nm in wavelength to not higher than $1/100$, the main part of the light components longer in wavelength than the stimulating light can be attenuated.

BRIEF DESCRIPTION OF DRAWINGS

FIG. 3 is a view showing properties of the longer wavelength light cut filter, FIGS. 4A to 4D are side views respectively showing variations of arrangement of the longer wavelength light cut filter, FIG. 5 is a side view showing a radiation image convertor panel in accordance with another embodiment of the present invention, and FIG. 6 is a side view showing a modification of the stimulating light beam projecting system.

DESCRIPTION OF THE PREFERRED EMBODIMENTS

Figure 1:
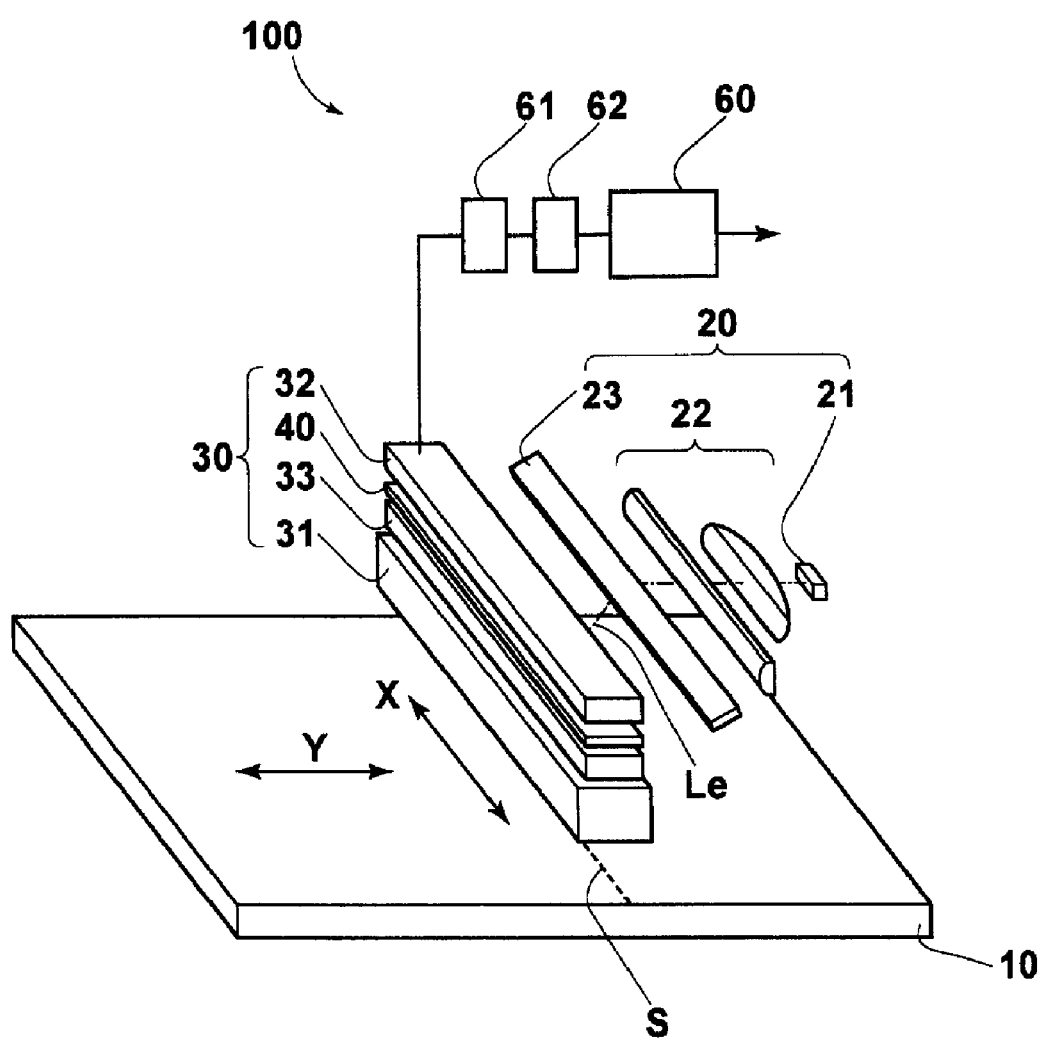
FIG. 1 is a perspective view briefly showing a radiation image read-out apparatus in accordance with an embodiment of the present invention.
Figure 2:
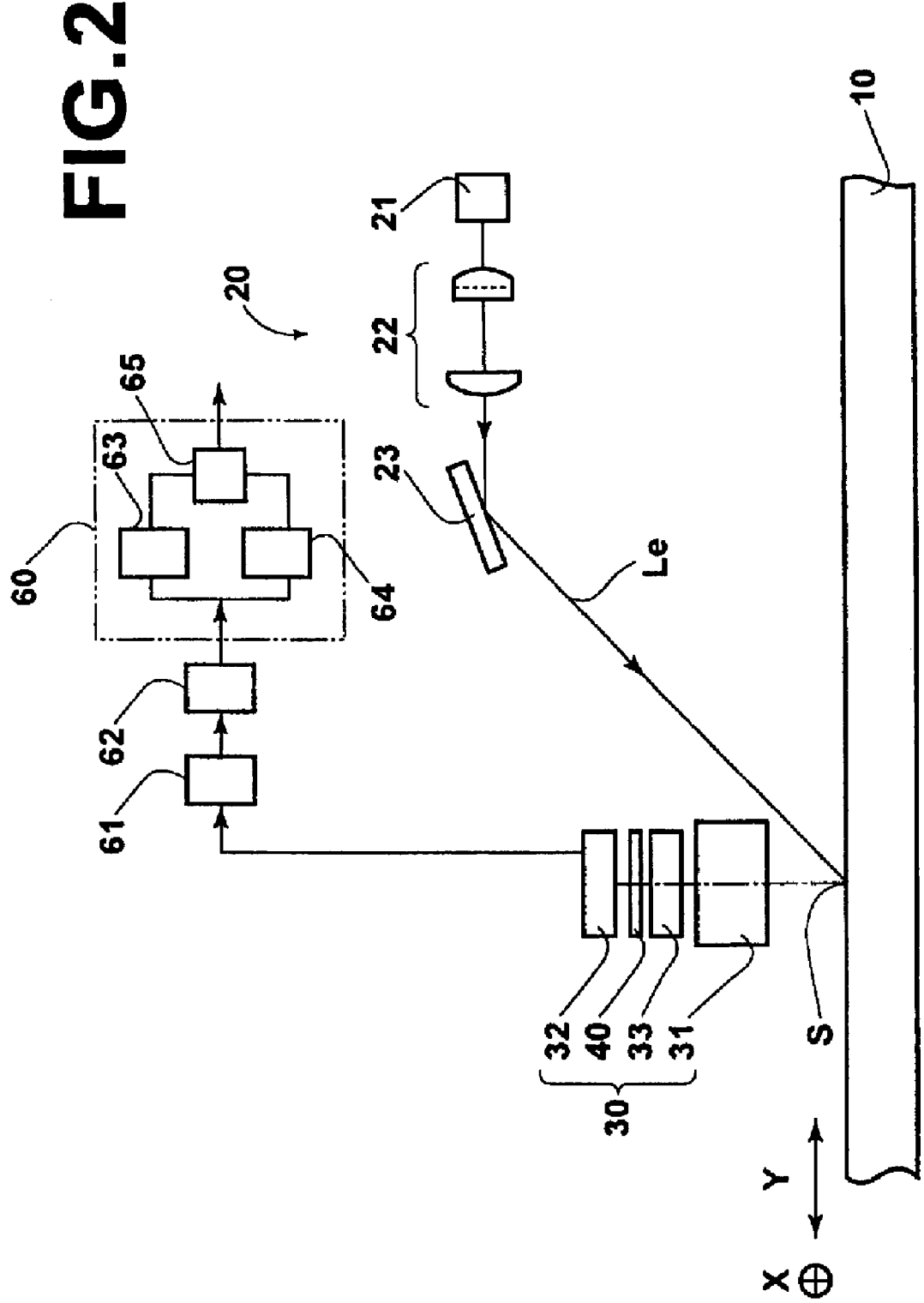
FIG. 2 is an enlarged side view showing the stimulating light beam projecting system and the detecting system employed in the radiation image read-out apparatus shown in FIG. 1.

In FIGS. 1 and 2, a radiation image read-out apparatus 100 in accordance with an embodiment of the present invention is for reading a radiation image recorded on a radiation image convertor panel 10 and comprises a stimulating light beam projecting system 20 which projects onto a radiation image convertor panel 10 a line-like stimulating light beam Le (660 nm in wavelength) extending in a main scanning direction X (the direction of arrow X in FIGS. 1 and 2), an imaging lens system 31 which condenses stimulated emission emitted from the radiation image convertor panel 10 upon exposure to the stimulating light beam Le, a line sensor 32 which comprises a plurality of photodiodes formed of material containing therein silicon as a main component and receives the stimulated emission imaged by the imaging lens system 31 to photoelectrically converting the stimulated emission to an electrical signal, a stimulating light cut filter 33 which is disposed in the optical path of the stimulated emission between the line sensor 32 and the radiation image convertor panel 10 to transmit the stimulated emission and to cut the stimulating light, a longer wavelength light cut filter 40 disposed in the optical path of the stimulated emission between the line sensor 30 and the radiation image convertor panel 10 to transmit the stimulated emission and attenuates the intensity of the light components longer in wavelength than the stimulating light, and an image signal correction means 60 which subtracts an image signal component which represents a light component longer in wavelength than the stimulating light LE passing through the longer wavelength light cut filter and is included in an image signal obtained by photoelectric conversion of the stimulated emission by the line sensor 32 from the image signal, thereby correcting the image signal.

The imaging lens system 31, the line sensor 32, the stimulating light cut filter 33 and the longer wavelength light cut filter 40 form a photodetector 30.

The stimulating light projecting system 20 comprises a broad area laser 21 which emits a stimulating light beam Le, a condenser optical system 22 which includes, for instance, a toric lens and converges the stimulating light beam Le in a line-like area extending in the main scanning direction X on the radiation image convertor panel 10 by way of a reflecting mirror 23, and projects onto the surface of the radiation image convertor panel 10 a line-like stimulating light beam Le.

The line sensor 32 comprises a number of CCDs arranged in the main scanning direction X. The imaging lens system 31 comprises, for instance, a number of refractive index profile type lenses arranged in the main scanning direction X and forms an erected image of the line-like area of the radiation image convertor panel 10 exposed to the stimulating light beam Le on the line sensor 32 at unit magnification.

The longer wavelength light cut filter 40 attenuates light components which are in a wavelength range W longer than a wavelength λ1 at which the intensity of the stimulating light is $\frac{1}{100}$ of the peak intensity of the stimulating light on the side longer in wavelength than the wavelength at which the stimulating light exhibits the peak intensity, in spectral distribution P which the stimulating light Le exhibits, within the range not longer than the longer side limit (1100 nm) of the sensitivity of the CCD. The longer wavelength light cut filter 40 may attenuate either a part (e.g., in a 100 nm width wavelength range) or the whole of the light components in the wavelength range W and is disposed between the imaging lens system 31 and the line sensor 32. For example, the longer wavelength light cut filter 40 attenuates the intensity of the light components in the range not shorter than 800 nm and not longer 900 nm in wavelength (the wavelength indicated at V in FIG. 3) to not higher than $\frac{1}{100}$.

An analog image signal as photoelectrically converted by the line sensor 32 is digitized into a digital image signal by an A/D convertor 61 and then the digital image signal is stored in an image buffer 62.

The image signal correction means 60 comprises an image memory G3 (FIG. 2) in which the digital image signal input from the image buffer 62 is temporarily stored, a longer light component generation system 64 which generates a longer light component signal component which represents light components longer in wavelength than the stimulating light Le and is estimated according to the digital image signal input from the image buffer 62, and a correction calculating system 65 which obtains a corrected image signal by subtracting the longer light component signal component input from the longer light component generation system 64 from the digital image signal input from the image memory 63.

The stimulating light projecting system 20 and the photodetector 30 are integrated with each other and are simultaneously conveyed in the sub-scanning direction Y (shown by arrow Y in FIGS. 1 and 2) by a conveyor means (not shown).

Operation of the radiation image read-out apparatus 100 of this embodiment will be described, hereinbelow.

A stimulating light beam Le emitted from the stimulating light projecting system 20 is converged in a line-like area S extending in the main scanning direction X on the radiation image convertor pane 110. The stimulated emission emitted from the line-like area S of the radiation image convertor panel 10 upon exposure to the stimulating light beam Le is imaged on the line sensor 32 through the imaging lens system 31, the stimulating light cut filter 33 and the longer wavelength light cut filter 40 and is photoelectrically converted and output as electric image signal components. While projecting the stimulating light beam Le and detecting the stimulated emission, the stimulating light projecting system 20 and the photodetector 30 are simultaneously conveyed by said conveyor means in the sub-scanning direction Y, whereby an image signal representing an image recorded on the radiation image convertor panel 10 is output from the line sensor 32.

The image signal output from the line sensor 32 is digitized by the A/D convertor 61 and the digital image signal is once stored in the image butter 62. The image memory 63 stores the digital image signal read out from the image buffer 62 and the longer light component generation system 64 generates a longer light component signal component estimated according to the digital image signal input from the image buffer 62. The correction calculating system 65 obtains a corrected image signal by subtracting the longer light component signal component input from the longer light component generation system 64 from the digital image signal input from the image memory 63.

For example, the longer light component signal component estimated according to the digital image signal input from the image buffer 62 generated by the longer light component generation system 64 may be extracted from a table representing the intensity of the stimulating light and the intensity of the light components of the stimulated emission longer in wavelength than the stimulating light which is stored in the longer light component generation system 64.

The longer wavelength light cut filter 40 may be formed, for instance, of color glass: C500 (HOYA)

FIGS. 4A to 4D show variations of arrangement of the longer wavelength light cut filter.

As denoted by 40A in FIG. 4A, the longer wavelength light cut filter may be disposed between the imaging lens system 31 and the radiation image convertor panel 10.

As denoted by 40B in FIG. 4B, the longer wavelength light cut filter may be in the form of a multi layer film applied to one of optical elements disposed in the optical path along which the stimulated emission emitted from the radiation image convertor panel propagates before it impinges upon the line sensor 32. When the longer wavelength light cut filter is in the form of a multilayer film, the longer wavelength light cut filter 40B can be integrated with another optical element and at the same time can be very small in thickness, whereby increase in the overall size of the radiation image read-out apparatus can be suppressed.

Further, as denoted by 40C in FIG. 4C, the longer wavelength light cut filter may comprise a flat plate which absorbs light components longer in wavelength than the stimulating light and is coated with a multilayer film absorbing light components longer in wavelength than the stimulating light and may be integrated with the stimulating light cut filter 33.

Further, as denoted by 33A in FIG. 4D, the stimulating light cut filter may double as the longer wavelength light cut filter.

Though, the longer wavelength light cut filter is provided on the radiation image read-out apparatus, the radiation image convertor panel may be provided with a longer wavelength light cut filter which transmits the stimulating light and the stimulated emission and attenuates the intensity of the light components longer in wavelength than the stimulating light on the side thereof from which the stimulated emission emitted from the radiation image convertor panel is detected as denoted by 10A in FIG. 5. In this case, it is preferred that the longer wavelength light cut filter doubles as a protective layer of the radiation image convertor panel.

Though, in the radiation image read-out apparatus of the embodiment described above, the photodetector comprises CCD elements, the present invention maybe applied to other radiation image read-out apparatuses where the photodetector comprises any other elements so long as the element has a sensitivity to light longer in wavelength than the stimulating light. For example, the photodetector may comprise a CMOS type or a VMIS type solid state image taking device.

Further, though, in the embodiment described above, the present invention is applied to a line-beam system radiation image read-out apparatus where a line-like stimulating light beam is projected onto the radiation image convertor panel and the stimulated emission emitted from the radiation image convertor panel upon exposure to the line-like stimulating light beam is detected by a line sensor, the present invention can be applied to a point-scan system radiation image read-out apparatus where a spot-like stimulating light beam is caused to scan the radiation image convertor panel in the main scanning direction, for instance, by a polygonal scanner, and stimulated emission emitted from the radiation image convertor panel in a time series upon exposure to the spot-like stimulating light beam is detected by a photodetector through a light guide, FIG. 6 shows a line-beam system radiation image read-out apparatus where the stimulating light beam projecting system is different from that shown in FIGS. 1 and 2. In FIG. 6, the stimulating light beam projecting system 20A comprises a stimulating light source 21A formed of a plurality of semiconductor lasers, each emitting a stimulating light beam Le, arranged in the main scanning direction X and a condenser optical system 22A formed of a cylindrical lens extending in the main scanning direction x which converges the stimulating light beam Le emitted from the stimulating light source 21A onto a line-like area S on a radiation image convertor panel 10A with a longer wavelength light cut filter.

As a photo detector comprising a diode having a sensitivity to light longer in wavelength than the stimulating light, there have been known those comprising a GaAsP photodiode or a hybrid CCD where a GaAsP sensor is provided in a CCD.

What is claimed is:

1. A radiation image read-out apparatus comprising a condenser optical system which converges stimulated emission emitted from a radiation image convertor panel upon exposure to stimulating light, a photodetector which receives the stimulated emission converged by the condenser optical system for photoelectric conversion and has a sensitivity to light longer in wavelength than the stimulating light, and a stimulating light cut filter which is disposed in the optical path of the stimulated emission between the photodetector and the radiation image convertor panel to transmit the stimulated emission and to cut the stimulating light and read out a radiation image recorded on the radiation image convertor panel, wherein the improvement comprises:

a longer wavelength light cut filter which transmits the stimulated emission and attenuates intensity of light components in the range not shorter than 800 nm and not longer 900 nm in wavelength provided in the optical path of the stimulated emission between the photodetector and the radiation image convertor panel; and a correction means which subtracts an image signal component which represents a light component longer in wavelength than the stimulating light passing through the longer wavelength light cut filter and is included in an image signal obtained by photoelectric conversion of the stimulated emission by the photodetector from the image signal, thereby correcting the image signal.

* * * * *